United States Patent [19]

Simmons

[11] Patent Number: 5,449,512

[45] Date of Patent: Sep. 12, 1995

[54] ANHYDROUS AFTER SHAVE LOTIONS

[75] Inventor: Mason S. Simmons, West Chester, Ohio

[73] Assignee: The Procter & Gamble Company, Cincinnati, Ohio

[21] Appl. No.: 295,188

[22] Filed: Aug. 24, 1994

[51] Int. Cl.⁶ .............................................. A61K 7/15
[52] U.S. Cl. ..................................... 424/73; 424/401; 514/847; 514/848
[58] Field of Search ........................... 424/70, 73, 401

[56] References Cited

U.S. PATENT DOCUMENTS

| | | | |
|---|---|---|---|
| 4,136,163 | 1/1979 | Watson et al. | 424/54 |
| 4,230,688 | 10/1980 | Rowsell et al. | 424/45 |
| 4,279,891 | 7/1981 | Henkel et al. | 424/73 |
| 4,758,599 | 7/1988 | Minetti | 514/844 |
| 4,761,278 | 8/1988 | Lewis et al. | 424/73 |
| 4,919,934 | 4/1990 | Deckner et al. | 424/401 |
| 4,985,459 | 1/1991 | Sunshine et al. | 514/561 |
| 5,160,494 | 11/1992 | Krzysik et al. | 512/3 |
| 5,286,476 | 2/1994 | Nanba et al. | 424/47 |

FOREIGN PATENT DOCUMENTS 666288 4/1967 South Africa .
93-25177 12/1993 WIPO .

OTHER PUBLICATIONS

Harrow, Philip A., "Shaving preparations in the patent literature 1970–1975", *Cosmetics and Toiletries*, vol. 91, Jul. 1976, pp. 18–20.
Dow Corning Trade Publications 1987 and 1990.
CTFA Cosmetic Ingredient Handbook, The Cosmetic and Toiletries Assoc., Inc. 1992, pp. 658–661, 572–580.

*Primary Examiner*—Thurman K. Page
*Assistant Examiner*—James M. Spear
*Attorney, Agent, or Firm*—John M. Howell; Anthony D. Sabatelli; Leonard W. Lewis

[57] ABSTRACT

The present invention are anhydrous after shave lotions comprising a perfume, an alcohol, and a low viscosity silicone fluid. Said compositions have less stinging and burning than compositions known in the art. Furthermore, said compositions are economical and have good skin feel characteristics.

3 Claims, No Drawings

ANHYDROUS AFTER SHAVE LOTIONS

TECHNICAL FIELD

The present invention is for anhydrous after shave lotions having superior skin feel upon application.

BACKGROUND OF THE INVENTION

After shave lotions, particularly those containing fragrances, are well known in the art. As used herein, after shave lotions are alcoholic compositions applied to the skin at any time in order to obtain desirable skin-feel characteristics.

Traditional after shave lotions contain significant levels of alcohol, typically from about 50% to about 90% ethanol, as described in U.S. Pat. No. 4,761,278, Lewis et al., issued Aug. 2, 1988 and U.S. Pat. No. 4,758,599, Minetti, issued Jul. 19, 1988; both herein incorporated herein by reference. While such lotions provide cooling and skin tightening, they also cause negative effects such as stinging and burning, particularly to skin having just been shaved with a razor blade.

Alcoholic after shave lotions containing ingredients to off-set these negative effects are known in the art. U.S. Pat. No. 4,758,599, Minetti, issued Jul. 19, 1988 discloses hydro-alcoholic after shave lotions providing moisturization and protection from infection while mitigating skin irritation. Said compositions disclosed therein combine from about 50% to 90% lower alcohols, niacinamide (a commonly known vasodilator), sodium lactate (a moisturizer), quaternuim 26 (an emollient), and water. In an attempt to mitigate stinging and burning without the use of ingredients such as vasodilators, after shave lotions were formulated having significantly reduced levels of alcohol. U.S. Pat 4,279,891, Henkel et al., issued Jul. 21, 1981 discloses clear after shave lotions containing from about 15% to about 20% ethanol, water, perfume, propylene glycol and ethoxylated alcohols, and betaine surfactant perfume solubilizer. These lotions require solubilizers to keep the perfume from separating from the low ethanol/water systems. Solubilization of perfumes in low ethanol ethanol/water based systems is disclosed in *The HLB System*, ICI Americas Incorporated, May 1992, incorporated herein by reference. These solubilizers, however, are responsible for skin irritation making these compositions less desirable.

South Africa Patent Application 666288, published Apr. 5, 1967 discloses anhydrous electric shaving aids including liquid compositions which offer users of electric razors an aid which helps to obtain a closer shave while tenderly treating the skin. Said compositions comprise at least 95% of a monovalent saturated aliphatic alcohol, up to 2.5% silicone oil and up to 2.5% of a cosmetically effective perfume which are incorporated in the composition without the use of emulsifiers. It is disclosed that these cosmetically effective perfumes may mainly be responsible for the fact that in spite of the high alcohol content, no symptoms of irritation have been found to occur.

U.S. Pat. No. 5,160,494, Krzysik et al, issued Nov. 3, 1992, incorporated herein by reference, discloses anhydrous, clear, emulsifier-free fragrance compositions comprising alcohol, perfume and volatile short chain alkylmethylsiloxane or a volatile cyclic alkylmethylsiloxane including those corresponding to the formulas

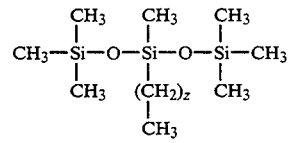

and

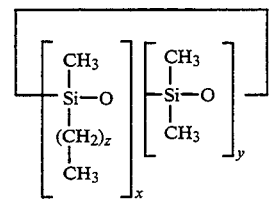

in which the sum of the integers x and y is four, five or six, with the proviso that x and y cannot be zero; and z is an integer having a value of 1–12. Said anhydrous compositions do not contain emulsifiers or solubilizers to incorporate the perfumes into said compositions which results in compositions having significantly reduces skin irritation. The level of alcohols in such compositions is from 40% to 90% of the compositions. In addition to the silicones disclosed above, Krzysik disclosed that the compositions therein may contain additional volatile silicones which include volatile methylsilicone fluids having the formula $(CH_3)_3SiO[(CH_3)_2SiO]_ySi(CH_3)_3$, wherein y is from zero to about 4. The examples disclosed therein shows compositions with cyclic, linear, and combinations of cyclic and linear alkylmethylsiloxanes with and without additional volatile methyl silicone fluids just disclosed. None of the examples disclosed therein contain only the additional volatile silicones just mentioned.

The additional volatile methyl silicone fluids disclosed in Krzysik include lower viscosity silicone oils disclosed by Dow Corning in their trade publications of 1987 and 1990 for Dow Corning 200, specifically 0.65 centistoke and 1.0 centistoke fluids. Said trade publications disclose that said fluids are useful in cosmetics compositions including fragrance compositions. Said fluids are soluble in ethanol and are non-greasy as well as non-stinging on the skin.

The present invention are anhydrous compositions wherein said compositions have superior skin feel when applied to the skin. Said compositions are less expensive than the compositions known in the art, and provide good skin care characteristics.

SUMMARY OF THE INVENTION

The anhydrous after shave composition comprising a fragrance, a $C_1$ to a $C_7$ monovalent alcohol, and a low viscosity silicone fluid having a formula:

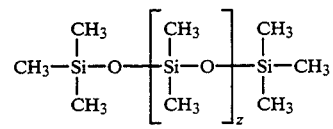

wherein z has a value from about 0 to about 3.

As used in the present invention anhydrous means that the composition may contain trace amounts of water, but, not so much as to require the use of an emulsifier to make a homogeneous composition. Typically trace amounts of water would include up to about 1.0%.

The compositions of the present invention have less stinging and burning than compositions known in the art. Furthermore, said compositions are economical and have good skin feel characteristics.

DETAILED DESCRIPTION OF THE INVENTION

A. Fragrances

The compositions of the present invention comprise a fragrance or perfume to impart a desired aroma, or to mask odors that may be associated with other components of the compositions. The particular fragrance selected is largely a matter of choice, however, the fragrance should be used at a level effective for providing a noticeable aroma to the composition, or for masking undesired aroma of the composition. The present invention comprises from about 0.1% to about 10%, preferably from about 0.1% to about 5.0%, and most preferably from about 2.0% to about 4.0% of a fragrance. Fragrances as used in the present invention are defined as volatile, odoriferous, component of one or more active fragrance compounds which exude pleasant or otherwise desired aromas at ambient conditions. The fragrances hereof are, in general, liquids at ambient temperature and are characterized by a flash point of from about 10° C. to about 120° C., more typically from about 25° C. to about 95° C. (as determined according to ASTM D-56 (c.c.)—Standard Test Method for Flash Point by Tag Closed Tester). The fragrance active compounds are typically incorporated into the fragrance components in liquid form, but can also be solids (such as the various camphoraceous fragrances known in the art) which are solubilized in other ingredients of the fragrance component.

The fragrances used in the present invention are active compounds which can include additional ingredients such as diluents, solvents for solid fragrance ingredients, and fixatives, etc. Diluents may or may not have their own aroma and, to the extent that they do, they are categorized as fragrance active compounds. Exemplary diluents and solvents include alcohols (e.g. ethyl alcohol, benzyl alcohol, dipropylene glycol, etc.) and liquid hydrocarbon and hydrocarbon esters (e.g. benzyl benzoate and other hydrocarbons and esters described above). Fixatives are ingredients which prolong the lasting quality of the fragrance upon use and can do so by modifying the overall volatility of the fragrance component. Some fixatives can function as fragrance active compounds, whereas others do not. To the extent that a particular ingredient performs both functions, it shall be considered a fragrance active compound. Exemplary fixatives include musk fragrance ingredients. A wide variety of fragrance active compounds are described in S. Arctander, Perfume, Flavors and Chemicals, Vols, I and II., Author, Montclair, N.J., the Merck Index, 8th Edition, Merck & Co., Inc., Rahway, N.J., and Secondini, Handbook of Perfumes and Flavors, Chemical Publishing Co., Inc., New York, N.Y., 1990 (ISBN) 0-8206-0334-1 ), incorporated herein by reference.

The fragrance will typically comprise a plurality of individual fragrance active compounds, although it can consist essentially of a single fragrance active compound. It is well within the scope of the fragrancer of ordinary skill in the art to change ingredients in the fragrance component and/or modifying the relative levels of fragrance ingredients.

Chemical compounds commonly known for use as a fragrance include phenolic compounds, essential oils, aldehydes, ketones, polycyclic compounds, esters and alcohols. Many Fragrance ingredients contain a combination of functional groups and can be categorized under two or more of the above classes.

From the standpoint of the fragrancer, it is convenient to consider the fragrance ingredients in terms of the type of aroma it imparts rather than the particular chemical class or classes it may fall within. The fragrance components herein can be formulated to provide a variety of odor categories: a non-exclusive list includes woody, sweet, citrus, floral, fruity, animal, spice, green, musk, balsamic, chemical and mint.

B. Alcohols

The compositions of the present invention comprise from about 10% to about 90%, preferably from about 20% to about 50%, and most preferably from about 20% to about 30% alcohol. The alcohol used in the present invention are $C_1$ to $C_6$ monohydric alcohols, preferably those selected from the group consisting of methanol, ethanol, propanol, isopropanol and mixtures thereof, most preferably ethanol. These alcohols provide cooling due their volatility and heat of vaporization, clean cosmetics due to their complete volatilization from the skin surface, solubilization of hydrophobic ingredients such as perfumes, and antisepsis. Trace amounts of water may enter the composition with the alcohol. For example anhydrous (200 proof) alcohols typically comprise 99.9% v/v alcohol and 0.1% water.

C. Low Viscosity Silicone Fluid

The compositions of the present invention comprise from about 10% to about 90%, preferably from about 40% to about 70%, and most preferably from about 50% to about 60% low viscosity silicone fluids. These low viscosity silicone fluids are linear methylsiloxanes selected from those having the formula

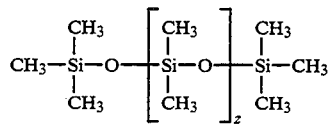

wherein z has a value from about 0 to about 3, preferably from about 0 to about 2, and most preferably from about 1 to about 2; with a viscosity of less than about 5.0 centistokes (hereinafter cs), preferably from about 0.5 cs to about 5.0 cs, most preferably from about 0.65 cs to about 1.0 cs measured at 25° C. at one atmosphere. Such linear methylsiloxanes are available from Dow Corning and are disclosed is their information publications from 1987 and 1990, incorporated herein by reference. Dow Corning 200 Fluids, specifically the very low viscosity or 0.65cs fluid and 1.0cs fluid are most preferred.

D. Optional Ingredients

The present invention may include a number of optional ingredients at levels necessary to achieve desirable compositional aesthetics, fragrance presentation, or skin feel and conditioning benefits to the skin. The following is a non-limiting disclosure of typical optional ingredients to be used together with the claimed invention. The composition of the present invention may contain, but are not limited to cosmetically active ingredients, medicaments and mixtures thereof to obtain desirable skin feel benefits. Cosmetically active ingredients are defined herein as compounds or materials which directly affect the appearance, feel, smell, or comfort of the skin, or which protect the skin from environmental factors (e.g. sun light). Medicaments are defined herein as compounds or materials that have a direct medicinal or neurological effect on the body (excluding $C_1$–$C_6$ alcohols). Such materials, well known in the art and are disclosed in the *CTFA Cosmetic Ingredient Handbook*, The Cosmetic, Toiletry, and Fragrance Association, Inc. 1992, pages 658–659.

Cosmetically Active Ingredients

Cosmetically active ingredients as used in the present invention includes coolants, skin conditioning agents selected from the group consisting of moisturizers, emollients, vitamins and mixtures thereof; sunscreens/pigments and mixtures thereof. Although the exact levels of these ingredients depend on the ingredient or combination of ingredients selected, typically cosmetically active ingredients are used at a levels from about 0.1% to about 40% of the composition.

a) Coolants

Coolants useful in the present invention herein are disclosed in PCT Application WO 93-05455, published Dec. 23, 1993; incorporated herein by reference. Said coolants include menthol, terpene alcohols and their derivatives, and carboxamides. Coolants that are particularly preferred include those disclosed in U.S. Pat. No. 4,230,688, Rowsell et al., issued Oct. 28, 1990 (Wilkinson Sword Limited, England) incorporated herein by reference; and 3-substituted-p-methanes as disclosed in U.S. Pat. No. 4,136,163 Watson et al., issued Jan. 23, 1979 (Wilkinson Sword Limited, England) incorporated herein by reference. Most preferred coolants used in the present invention are N,2, 3trimethyl2-isopropulbutanamide, N-ethyl p-methan-3-carboxamide,and mixtures thereof, at levels from about 0.05% to about 1.0% of the composition.

b) Skin Conditioning Agents

Skin conditioning agents are also useful in the present invention to provide the user with desirable characteristics such as good glide over the skin upon application, dry feeling, smooth skin after dry down, and soft skin. Typical skin conditioning agents as found *CTFA Cosmetic Ingredient Handbook*, The Cosmetic, Toiletry and Fragrance Association. Inc. pp.572–580, incorporated herein by reference. Said skin conditioning agents which may be used in the present invention include moisturizers, emollients, vitamins and mixtures thereof.

(1) Moisturizers, also referred to in the present invention as humectants, include urea, guanidine, glycolic acid and glycolate salts (e.g. ammonium and quaternary alkyl ammonium), lactic acid and lactate salts (e.g. ammonium and quaternary alkyl ammonium), aloe vera in any of its variety of forms (e.g. aloe vera gel), polyhydroxy alcohols (such as sorbitol, glycerol, hexanetriol, propylene glycol, hexylene glycol and the like), polyethylene glycol, sugars and starches, sugar and starch derivatives (e.g. alkoxylated glucose), hyaluronic acid, lactamide monoethanolamine, acetamide monoethanolamine, and mixtures thereof.

(2) Emollients useful in the instant invention are further described in U.S. Pat. No. 4,919,934, Deckner et al., issued Apr. 24, 1990, incorporated herein by reference. The emollients are used at levels from about 1% to about 10% by weight of the composition. Said emollients include, but are not limited to, volatile and nonvolatile silicone oils, hydrocarbon oils, long chain esters having at least 10 carbon atoms, and mixtures thereof. The preferred emollients are nonvolatile silicone fluids.

Nonvolatile silicone fluids as used herein generally have average viscosities of at least about 1,000 cs, preferably from about 1,000 to about 2,000,000 cs more preferably from about 10,000 to about 1,800,000 cs, even more preferably from about 100,000 to about 1,500,000 cs at 25° C. Lower viscosity nonvolatile silicone conditioning agents with a minimum viscosity of about 50 cs, can also be used as can volatile cyclic silicones such as, but not limited to octamethylcyclotetrasiloxane, decamethylcyclopentasiloxane, and mixtures thereof.

The hydrocarbon oils include esters with hydrocarbyl chains derived from fatty acids or alcohols (e.g. mono-esters, polyhydric alcohol esters, and di- and tri-carboxylic acid esters). The hydrocarbyl radicals of the fatty esters hereof can also include or have covalently bonded thereto other compatible functionalities, such as amides and alkoxy moieties (e.g. ethoxy or ether linkages). Hydrocarbon oils include saturated or unsaturated cyclic hydrocarbons, straight chain aliphatic hydrocarbons, and branched chain aliphatic hydrocarbons. Straight chain hydrocarbon oils will preferably contain from about 12 to about 19 carbon atoms. Branched chain hydrocarbon oils typically may contain higher numbers of carbon atoms. Specific examples include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane such as 2, 2, 4, 4, 6, 6, 8, 8-dimethyl-10-methylundecane and 2, 2, 4, 4, 6, 6-dimethyl-8-methylnonane, sold by Permethyl Corporation.

Long chain fatty esters include, for example, alkyl and alkenyl esters of fatty acids having aliphatic chains with from about 10 to about 22 carbon atoms, and alkyl and alkenyl fatty alcohol carboxylic acid esters having an alkyi and/or alkenyl alcohol-derived aliphatic chain with about 10 to about 22 carbon atoms, and combinations thereof.

3) Vitamins and vitamin derivatives are useful as skin conditioning agents in the present invention particularly in light of the fact that some vitamin and vitamin derivatives are incompatible in water based systems. Vitamins useful in the present invention are generally disclosed in *The Condensed Chemical Dictionary*, Van Nostrand Reinhold Company, Ninth Edition, pp. 920–921, and Idson, *Vitamins and the Skin*, Cosmetics and Toiletries Vol. 108, pp. 79–94, December 1993, incorporated herein by reference. A non-limiting example of vitamins that are useful in the present invention is Vitamin E Acetate which is practically water insoluble but is readily soluble in the present invention.

c) Sunscreens and Pigments

Sunscreens and pigments for coloring the skin or aid in tanning of the skin may be used in the present invention and are generally disclosed in U.S. Pat. No. 5,087,445, Haffey et al., issued Feb. 11, 1992; U.S. Pat. No. 5,073,372, to Turner et al., issued Dec. 17, 1991; and Segarin et al., Cosmetics Science and Technology, Chapter VIII, pages 189 et seq., all of which are incorporated herein by reference. Generally, the sunscreens can comprise from about 0.5% to about 20% of the compositions useful herein. Exact amounts will vary depending upon the sunscreen chosen and the desired Sun Protection Factor (SPF). SPF is a commonly used measure of photo protection of a sunscreen against erythema. See Federal Register, Vol. 43, No. 166, pp. 38206–38269, Aug. 25, 1978, incorporated herein by reference.

Preferred among those sunscreens disclosed in the above references are those selected from the group consisting of ethylhexyl p-methoxycinnamate, octocrylene, octyl salicylate, oxybenzone, and mixtures thereof. Other useful sunscreens include the solid physical sun blocks such as titanium dioxide (e.g. micronized titanium dioxide, 0.03 microns), zinc oxide, silica, iron oxide and the like. Still other useful sunscreens are those disclosed in U.S. Pat. No. 4,937,370, Sabatelli, issued Jun. 26, 1990 and U.S. Pat. No. 4,999,186, Sabatelli et al., issued Mar. 12, 1991; both incorporated herein by reference.

Medicaments

The medicaments used in the present invention include, but are not limited to, anti-acne ingredients, antibiotics, anti-microbials, anti-fungals, anti-vitals, anti-bacterials, anti-protozols, anti-inflammatory actives, astringents, antiseptics. Such materials are well known for making compositions at levels to achieve the intended medical effect at the expected unit dosage. The medicaments are preferably used at levels of about 0.1% to about 10% by weight of the composition.

Anti-acne ingredients such as salicylic acid and anti-inflammatory ingredients such as pantothenic acid, pantothenic acid derivatives (e.g., alcohol, aldehyde, alcohol ester, acid ester derivatives, especially alcohol derivatives such as panthenol), α racemic bisabolol, trimethylglycine, and mixtures thereof are particularly useful in the present invention. Examples of other medicaments include keratolytics such as sulfur, lactic acid, glycolic, pyruvic acid, urea, resorcinol, and N-acetylcysteine; retinoids such as retinoic acid and its derivatives (e.g., cis and trans); antibiotics, antimicrobials, antibacterials, antifungals, antiprotozoals, and antivirals (e.g., benzoyl peroxide, octopirox, erythromycin, tetracyclin, triclosan, azelaic acid and its derivatives, phenoxy ethanol and phenoxy proponol, ethylacetate, clindamycin and meclocycline, triclosan, chlorhexidine, tetracycline, neomycin, miconazole hydrochloride, octopifox, parachlorometaxylenol, nystatin, tolnaftate, clotrimazole, and the like; sebostats such as flavinoids; hydroxy acids; antipruritic drugs including, for example, pharmaceutically-acceptable salts of methdilizine and trimeprazine; and bile salts such as scymnol sulfate and its derivatives, deoxychloate, and cholate.

Also, useful are non-steroidal anti-inflammatory drugs (NSAIDS). The NSAIDS can be selected from the following categories: propionic acid derivatives, acetic acid derivatives, fenamic acid derivatives, biphenylcarboxylic acid derivatives, and oxicams. All of these NSAIDS are fully described in the U.S. Pat. No. 4,985,459 to Sunshine et al., issued Jan. 15, 1991, incorporated by reference. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofin, tiaprofenic acid, fluprofen and bucloxic acid. Also useful are the steroidal anti-inflammatory drugs including hydrocortisone and the like.

EXAMPLES

The following examples serve to further describe and demonstrate embodiments within the scope of the invention, but are not to be construed as limitations of the present invention as many variations are possible without departing from the spirit of the invention. The scope of the invention is defined in the claims which follow.

| Ingredient (wt. %) | Examples | | | | |
|---|---|---|---|---|---|
| | 1 | 2 | 3 | 4 | 5 |
| Silicone Fluid[1] | 10.0 | 50.0 | 70.0 | 84.0 | 72.0 |
| Alcohol[2] | 89.9 | 45.0 | 20.0 | 10.0 | 24.0 |
| Fragrance | 0.1 | 5.0 | 10.0 | 6.0 | 4.0 |

[1] Dow Corning Fluid 200 1.0 cs, available from Dow Corning Corporation, Midland, MI.
[2] Ethyl Alcohol SD 40-2 (200 proof), available from Shell Chemical Company, Houston, TX.

The compositions of the above examples are prepared by combining the ingredients in a vessel equipped with mixing, stirring said combination until uniform.

| Ingredient (wt. %) | Examples | | | | | | |
|---|---|---|---|---|---|---|---|
| | 6 | 7 | 8 | 9 | 10 | 11 | 12 |
| Silicone Fluid[1] | 55.77 | 39.4 | 67.5 | 74.52 | 65.0 | 18.25 | 44.45 |
| Alcohol[2] | 30.0 | 45.0 | 20.0 | 10.0 | 25.0 | 70.0 | 30.0 |
| Fragrance | 3.0 | 5.0 | 10.0 | 6.0 | 3.0 | 5.0 | 2.5 |
| Emollient I[3] | 3.0 | 5.0 | 1.0 | 6.5 | 2.5 | 2.0 | 2.0 |
| Emollient II[4] | 4.0 | — | 1.0 | — | 4.0 | 2.0 | 1.0 |
| Emollient III[5] | — | — | — | — | — | — | 17.5 |
| Vitamin E Acetate | 2.0 | 4.0 | — | 1.0 | 0.5 | 1.0 | 0.5 |
| Salicylic Acid | 2.0 | 1.5 | 0.5 | 1.75 | — | 1.5 | 1.75 |
| Coolant I[6] | 0.15 | 0.05 | — | 0.15 | — | 0.1 | 0.2 |
| Coolant II[7] | 0.08 | 0.05 | — | 0.08 | — | 0.15 | 0.1 |

[1] Dow Corning Fluid 200 1.0 cs, available from Dow Corning Corporation, Midland, MI.
[2] Ethyl Alcohol SD 40-2 (200 prooo, available from Shell Chemical Company, Houston, TX.
[3] Isopropyl Myristate
[4] Mineral Oil
[5] Decamethylcyclopentasiloxane
[6] N,2,3,-trimethyl-2-isopropulbutanamide
[7] N-ethyl p-methan-3-carboxamide The compositions disclosed in said examples are prepared by dissolving the Salicylic Acid, Coolant I and II, Vitamin E Acetate in the Alcohol in a vessel equipped with mixing. The Fragrance, Emollient I, II and III, and Silicone Fluid are added sequentially to the above combination and mixing the combination until uniform.

What is claimed is:

1. An anhydrous after shave lotion comprising:
   a. from about 0.1% to about 10% of a perfume;
   b. from about 10% to about 90% of a $C_1$ to a $C_6$ monohydric alcohol;
   c. from about 10% to about 90% of a linear methylsiloxane having a formula:

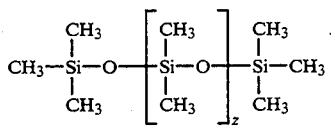

wherein z has a value from about 0 to about 3, and the viscosity of said silicone fluid is less than about 5 cs; and d. a skin coolant selected from the group consisting of N-2,3,-trimethyl-2-isopropylbutanamide, N-ethyl p-methan-3-carboxamide and mixtures thereof.

2. An anhydrous after shave lotion comprising:

a. from about 0.1% to about 5% of a perfume;

b. from about 20% to about 50% of a $C_1$ to a $C_6$ monohydric alcohol;

c. from about 40% to about 70% of a linear methylsiloxane having a formula:

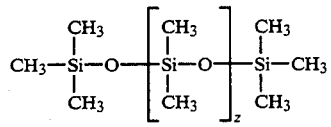

wherein z has a value from about 0 to about 2, and the viscosity of said silicone fluid is from about 0.5 cs to about 5.0 cs;

d. from about 0.05% to about 1% of a coolant;

e. from about 0.1% to about 40% of a skin conditioning agent selected from the group consisting of moisturizers, emollients, vitamins, and mixtures thereof; and f. from about 0.1% to about 10% of a medicament.

3. An anhydrous after shave lotion comprising:

a. from about 2.0% to about 4.0% of a perfume;

b. from about 20% to about 30% ethanol;

c. from about 50% to about 60% of a linear methylsiloxane having a formula:

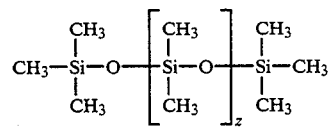

wherein z has a value from about 1 to about 2, and the viscosity of said silicone fluid is from about 0.65 cs to about 1.0 cs;

d. from about 0.05% to about 1.0% of a skin coolant selected from the group consisting of N,2, 3,-trimethyl-2-isopropyl butanamide, N-ethyl p-methan-3-carboxamide,and mixtures thereof;

e. from about 1% to about 10% of an emollient; and f. from about 0.5% to about 2.0% salicylic acid.

* * * * *